United States Patent [19]

Torrisi et al.

[11] Patent Number: 5,323,441
[45] Date of Patent: Jun. 21, 1994

[54] SAMPLE HOLDER FOR SPECTROSCOPIC ANALYSIS AND METHOD FOR MOUNTING FILM TO SAMPLE HOLDER

[75] Inventors: Angelo M. Torrisi, 10 Anpell Dr., Scarsdale, N.Y. 10583; Roland Urbano, Tuckahoe, N.Y.

[73] Assignee: Angelo M. Torrisi, Tuckahoe, N.Y.

[21] Appl. No.: 991,026

[22] Filed: Dec. 15, 1992

[51] Int. Cl.⁵ ............................................. G01N 23/10
[52] U.S. Cl. ..................................... 378/44; 378/208; 356/246
[58] Field of Search .................... 378/44, 45, 47, 208; 356/246

[56] References Cited

U.S. PATENT DOCUMENTS

| | | | |
|---|---|---|---|
| 4,037,109 | 7/1977 | Hosokawa et al. | 378/45 |
| 4,448,311 | 5/1984 | Houser | 378/208 |
| 4,575,869 | 3/1986 | Torrisi et al. | 378/47 |
| 4,587,666 | 5/1986 | Torrisi et al. | 378/47 |

Primary Examiner—David P. Porta
Attorney, Agent, or Firm—Paul J. Sutton

[57] ABSTRACT

A sample holder for positioning and locking film for sample materials for spectroscopic analysis comprising a holder body having a cylindrical outer wall forming a cell adapted to contain the sample material and a ring member for biasedly pressing the film skirt against the cylindrical outer wall of the holder body in a first locking position. A locking bead around the ring member presses the film skirt into a locking groove around the cylindrical wall of the holder body in a second locking position. An optional third locking position is attained by a second locking bead around the biasable ring member pressing the film skirt into a second locking groove around the holder body. A method of assembling the film with the holder body and the ring member is also described.

13 Claims, 4 Drawing Sheets

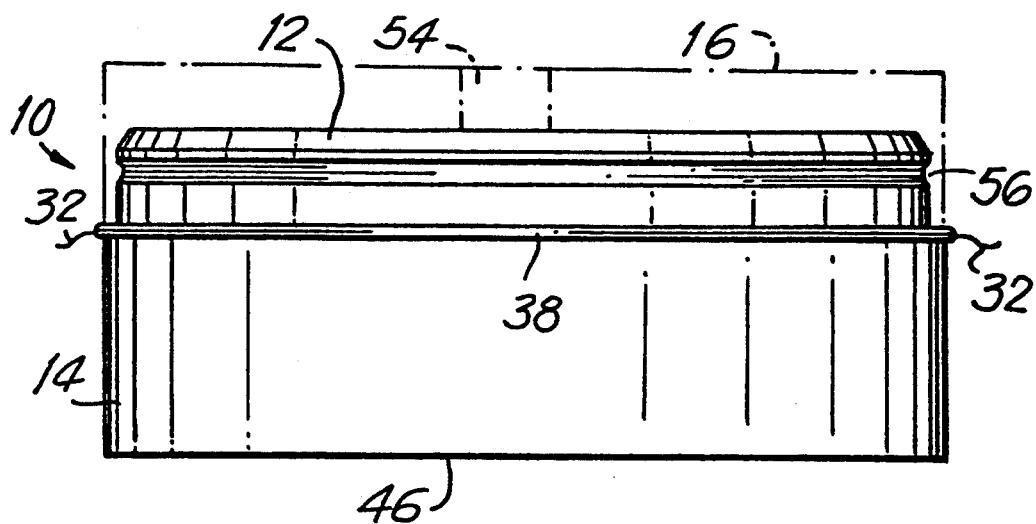
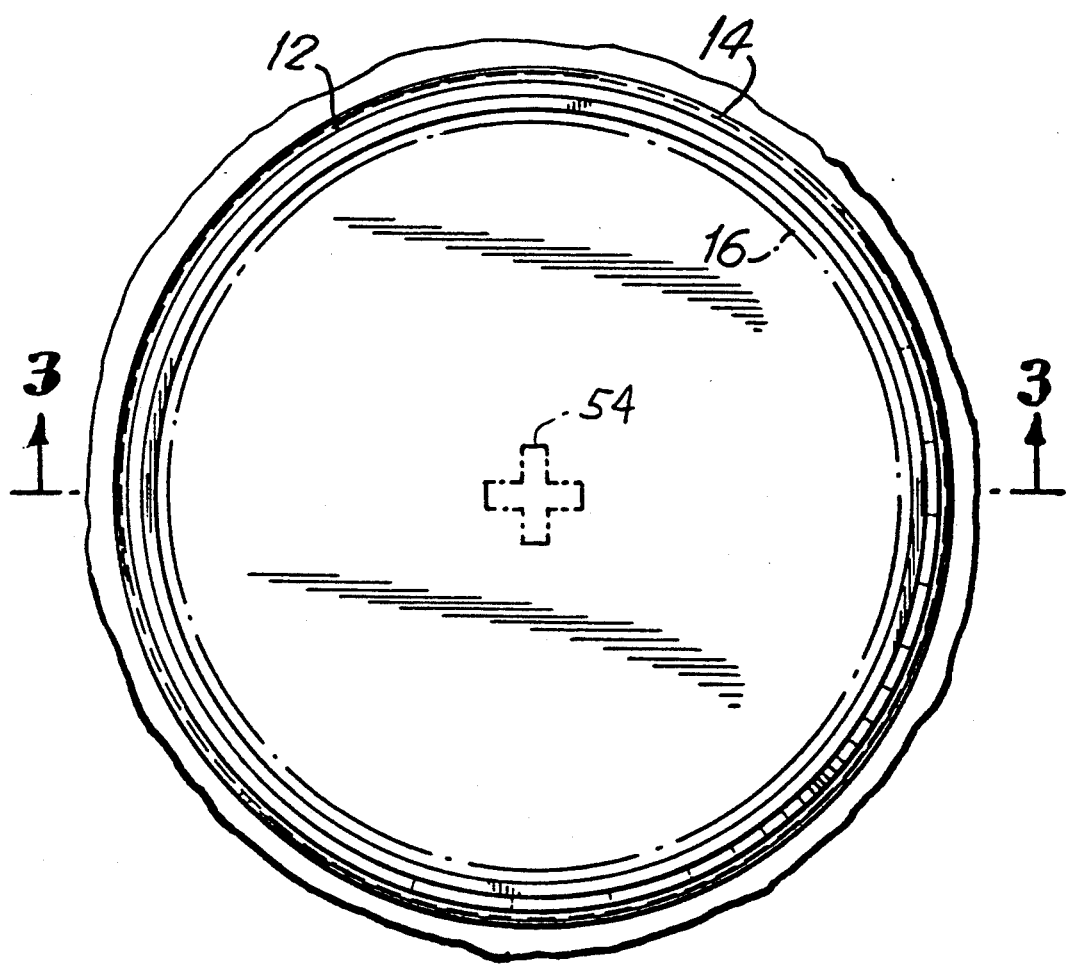

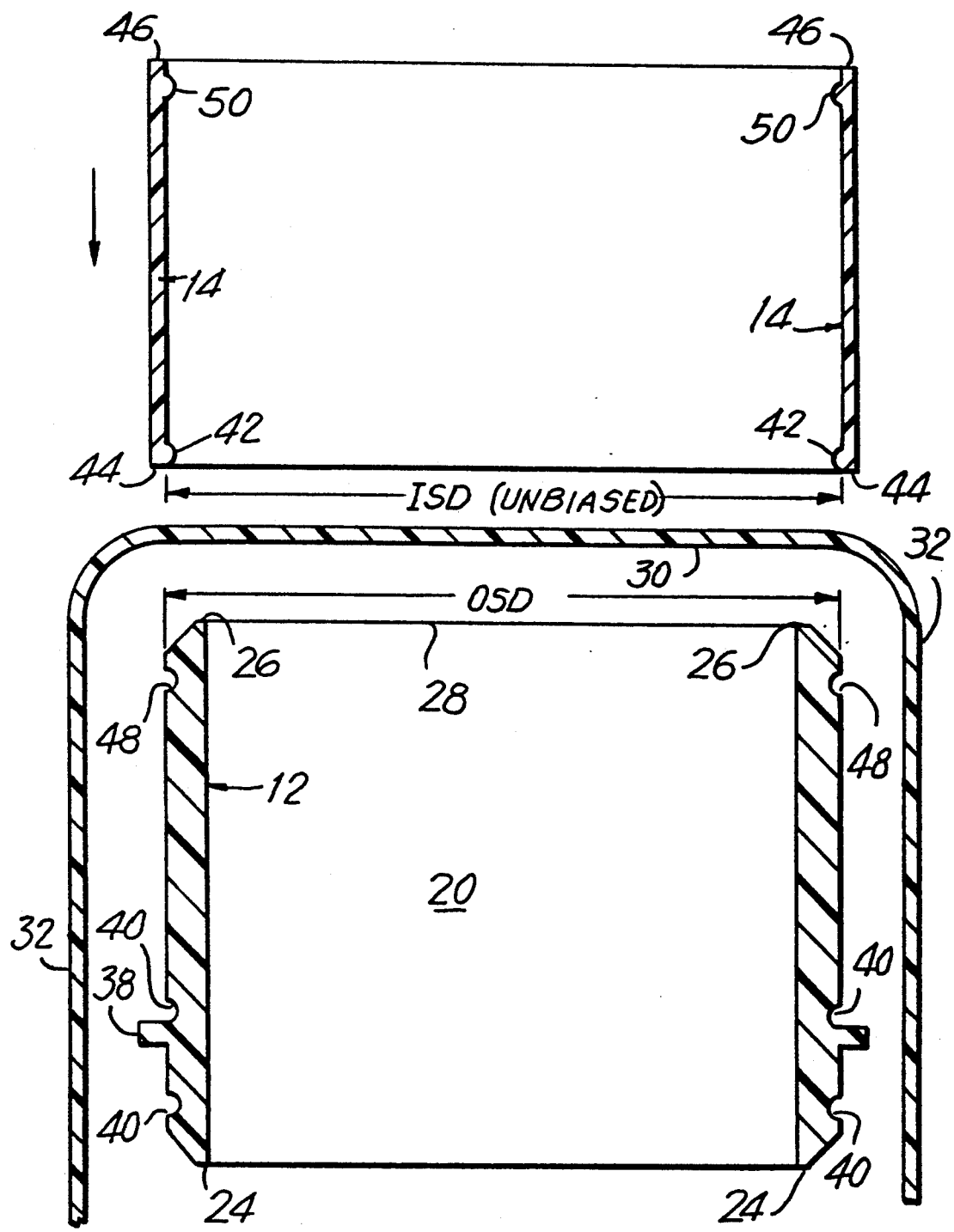

SAMPLE HOLDER FOR SPECTROSCOPIC ANALYSIS AND METHOD FOR MOUNTING FILM TO SAMPLE HOLDER

FIELD OF THE INVENTION

This invention relates generally to the field of disposable sample holders for X-ray spectroscopic analysis and more particularly to a film locking system and a method for securing the film to the sample holder.

BACKGROUND OF THE INVENTION

The field of spectroscopy involves the measurement of the spectra of certain material being analyzed. Without going into detail here, which is well-known to those familiar with the art, it can in summary be said that an atom releases a quantum of energy that emits a particular wave length of the electromagnetic spectrum where bombarded by X-rays or at times by other regions of the electromagnetic spectrum.

The field of spectroscopy is that of high precision technology. The X-ray apparatus that is used to read or interpret the sample is finally dependent upon the quality of the presentation and preparation of the sample being analyzed because a precise geometry of distance is involved in the measurement process. Also, because of X-ray absorption factors, polyethylene or polypropylene films employed as X-ray transparent windows are fragile and very thin, ranging in thicknesses as low as between 0.00005 in. (0.0012 mm) to 0.00050 in. (0.013 mm).

A sample is positioned in a cylindrical sample holder that includes a holder body forming a cell adapted to contain the sample. A disposable sample holder is generally made of polyethylene or polypropylene and is generally intended to be discarded after a single use. A sample holder will range in size between diameters of 0.39 in. to 2.25 in. (1 mm to 57 mm) and have a height of about 1 in. (25 mm), although these dimensions will vary.

The first phase of the analysis is in the support and presentation of the sample for spectroscopy. In one type of holder, a very thin plastic film is placed taut as an X-ray transparent window across the circular end face of the body of the holder, and the skirt of the film is then secured to the outer wall of the body. The body is then inverted so that the window film face is positioned downwards. The holder cell is thereupon filled with the sample through the top open face of the holder body. A cap, which is not always necessary, can then be placed on the top open face to close the cell and form a complete holder of a body with a cap. The sample holder is then placed in a cell positioner of the particular spectroscopic apparatus being used, and the electromagnetic waves are applied upwardly to the downwardly positioned film face of the holder upon which the sample material is lying. The X-ray analysis may be conducted in an air, inert gas, or vacuum environment. The type of cap used, when a cap is necessary, varies in accordance with the environment and the type of sample being analyzed.

The precise geometry of distance encompassed by spectroscopic analysis is dependent upon the integrity of the film face that is tautly stretched across the bottom face of the cell of the holder. The sample material in the cell lies upon the film, which must retain a perfectly flat horizontal face, which in turn creates a perfectly flat surface of the sample material lying on the film. In addition the film must maintain a tight pressure fit around the base of the holder so as to create a seal that prevents any leakage of sample material, particularly a liquid or volatile sample, from the cell. Also, the thermal coefficient of the film and the sample can change considerably under the heat generated by the X-ray bombardment inducing shrinkage and/or expansion creating stress on the film.

Also, film can shrink or expand because of heat generated by X-ray bombardment. The coefficient of expansion of the film and the sample may vary, thus creating stress on the film.

DESCRIPTION OF THE PRIOR ART

The achievement of a tight fit of film across the open face of the cell of the holder has been attempted in the art in various ways. At one time a common means of doing this was by securing the skirt of the film by a pressure fit of an O-ring snap-in mounted into a slot of the upper annular outer area of the holder body with the skirt of the film wedged into the snap-in slot between the O-ring and the upper annular holder body.

Another means of achieving and maintaining film tautness and sealing is to place a thick-walled, rigid cylindrical ring member around the skirt of the film in combination with the O-ring. The rigid ring member is placed around the base of the holder body so that it presses the film tightly across the face of the body. The rigid member ring is placed around the O-ring, which further secures the skirt of the film. The rigid ring member is locked to the body preferably by a snap-in connection. The problem with this type of film support is that it may exert excessive force upon the thin film and cause it to rupture.

An improved means for achieving and maintaining film tautness and sealing is set forth in U.S. Pat. No. 4,587,666 issued on May 6, 1986 to Torrisi and Urbano. This system includes a flexible, tapered cylindrical member snap-in mounted over a matching tapered portion of an annular outer wall of the holder body so that a first portion of the skirt of the film is pressed against the tapered annular wall. An outer cylindrical closure sleeve snap-in mounted to the annular wall of the holder body secures additional portions of the film skirt against the annular wall. A rim flange of the closure sleeve holds the ring member in position. An optional O-ring snap-in mounted to the annular wall of the holder body presses another portion of the film skirt to the holder body.

U.S. Pat. No. '666 can be improved on to the extent that the holder body, the tapered annular wall, and the closure body described therein constitute three separate elements with the optional O-ring increasing the total to four elements, which tends to decrease the efficiency of the film mounting operation.

SUMMARY OF THE INVENTION

It is therefore an object of the present invention to provide a sample holder for sample materials for spectroscopic analysis that more efficiently mounts and positions film tautly yet gently across an open face of the film holder.

It is another object of the present invention to provide a gentle, firm, film positioning, handling, and locking system for sample holder film that tautens the skirt of the film against the lower face of the holder by provision of a single locking element in combination with he holder body.

It is still another object of the present invention to provide a sample holder for materials for spectroscopic analysis that includes an outer cylindrical ring member that biasedly presses and holds film to a cylindrical holder body over the entire cylindrical inner surface of the ring member to a substantial area of the outer cylindrical surface of the holder body.

It is yet another object of the present invention to provide a sample holder for materials for spectroscopic analysis that biasedly locks the film with the sample holder in at least two locking positions and at an optional third locking position.

In accordance with these and other objects that will become apparent in the course of this disclosure, there is provided a sample holder for positioning and locking film for sample materials for spectroscopic analysis comprising a holder body having a cylindrical outer wall forming a cell adapted to contain the sample material and a cylindrical ring member for biasedly pressing the film skirt against the cylindrical outer wall of the holder body in a first locking position. A bead within the ring member presses the film skirt into a groove formed around the cylindrical outer wall of the holder body in a second locking position. An optional third locking position is attained by a second bead within the biasable ring member pressing the film skirt into a second groove formed around the holder body. A method of assembling the film with the holder body and the ring member is also described.

The present invention will be better understood and the objects and important features, other than those specifically set forth above, will become apparent when consideration is given to the following details and description, which when taken in conjunction with the annexed drawings, describes, discloses, illustrates, and shows preferred embodiments or modifications of the present invention and what is presently considered and believed to be the best mode of practice in the principles thereof.

BRIEF DESCRIPTION OF THE DRAWINGS

The invention will be more clearly understood from the following figures setting forth a specific embodiment of the invention:

FIG. 1 is an elevational view of the sample holder in accordance with the present invention with an optional cap shown in phantom line.

FIG. 2 is a top view of the sample holder illustrated in FIG. 1;

FIG. 5 is a view of the invention with the elements positioned immediately prior to the mounting of the film to the body holder with the film positioned between the holder body and the ring member with all the element in sectional view analogous to the view of FIG. 3.

DESCRIPTION OF THE PREFERRED EMBODIMENT

Figure 3:
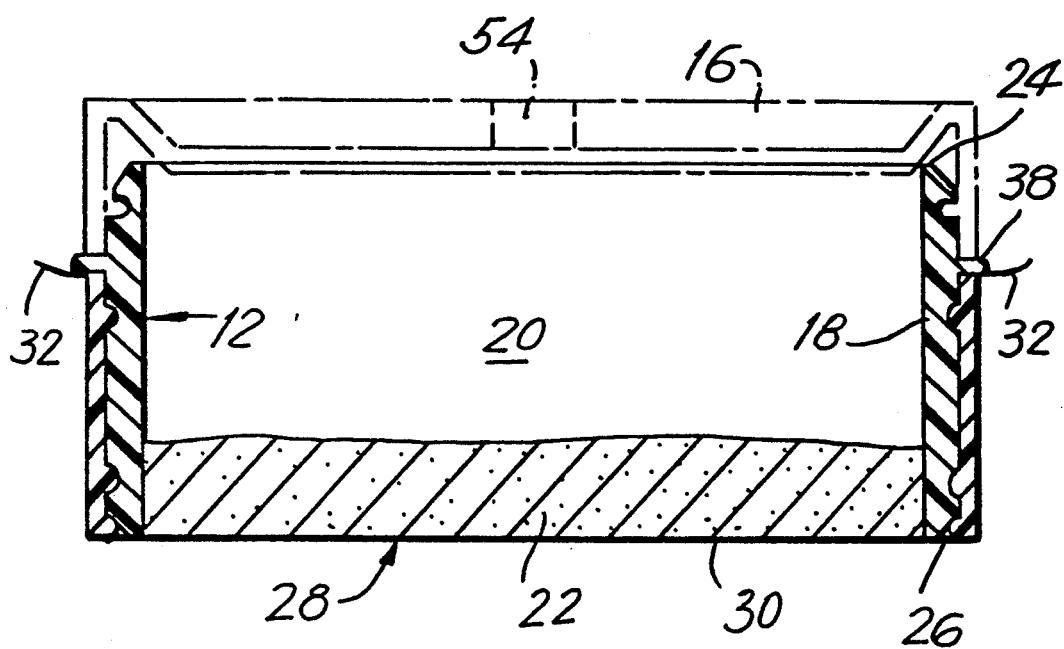
FIG. 3 is a sectional view taken through line 3—3 of FIG. 2.

Reference is now made in detail to the drawings wherein the same reference numerals refer to the same or similar elements throughout.

FIGS. 1 and 2 illustrate a sample holder 10 for holding sample materials for spectroscopic analysis that includes a cylindrical holder body 12 surrounded by a cylindrical ring member 14. An optional cap 16 is snap-in mounted to the top of sample holder 10. Body 12 includes a cylindrical wall 18 forming a cell 20 that contains a sample material 22, shown as a particulate material for purposes of exposition but which can be a liquid or a gas. Wall 18 has first and second circular edges 24 and 26, respectively, shown in FIGS. 3 and 4 with first edge 24 the upper side edge and second edge 26 the lower side edge. Second edge 26 defines an open face 28 of cell 20. A thin, transparent, plastic film 30 is positioned around second edge 26 and across open face 28 for sealing open face 28 so as to prevent the passage of sample material 22 from cell 20. Film 30 maintains a taut surface across open face 28 for sample material 22 for analysis. Film 30 includes a film skirt 32 that engages cylindrical wall 18 of holder body 12.

Ring member 14 is cylindrical and biasable having a cylindrical inner surface 34. In the mounted position around holder body 12 shown in FIGS. 1, 2, 3, and 4, ring member 14 is in a biased mode that biasedly presses film 30 in a first locking position wherein ring member 14 by way of cylindrical inner surface 34 presses film skirt 32 against cylindrical wall 18, in particular cylindrical outer surface 36, of holder body 12. For the purposes of this application, cylindrical means having the forms of a cylinder, and cylinder means the surface traced by a straight line moving parallel to a fixed straight line and intersecting a planar closed curve. In the embodiment illustrated in FIGS. 1-5 the curve is that of a circle. Thus, the surface over which film skirt 32 is pressed by cylindrical outer surface 36 against cylindrical inner surface 34 is the entire cylindrical inner surface 34 against a large area of the total surface area of cylindrical outer surface 36.

An annular stop flange 38, which extends radially outwardly from cylindrical outer surface 36 of holder body 12, prevents ring member 14 from being moved axially inwardly away from second edge 26 towards first edge 24.

Ring member 14 also biasedly presses film skirt 32 against cylindrical wall 18 in a second locking position. In particular, holder body 12 includes cylindrical outer surface 36 defining an annular locking groove 40 and ring member 14 including an annular locking bead 42 extending radially inwardly from cylindrical inner surface 34. Bead 42 is snap-in mounted into locking groove 40 so that film skirt 32 is pressed into groove 40 by bead 42. Ring member 14 has opposed first and second circular edges 44 and 46, respectively, oriented as the upward side and lower side edges, respectively, in FIGS. 1-4 with bead 42 being coextensive with first edge 44, which in turn is adjacent to stop flange 38. The second locking position of groove 40 and bead 42 prevents ring member 14 from moving axially in either direction relative to first and second edges 24 and 26 of holder body 12 from the mounted position around cylindrical wall 18 of holder body 12.

Ring member 14 also biasedly presses film skirt 32 against cylindrical wall 18 in a third locking position. In particular, holder body 12 includes cylindrical outer surface 36 defining an annular groove 48 and ring member 14 including an annular bead 50 extending radially inwardly from cylindrical inner surface 34. Bead 50 is snap-in mounted into groove 48 so that film skirt 32 is pressed into groove 48 by bead 50. Bead 50 is proximate to second circular edge 46 of ring member 14; and groove 48 is proximate to second circular edge 26 of holder body 12. The third locking position of groove 48 and bead 50 prevents ring member 14 from moving axially in either direction relative to first and second edges 24 and 26 of holder body 12 from the mounted position around cylindrical wall 18 of holder body 12.

Second cylindrical edge 26 at open face 28 of holder body 12 forms an outwardly and downwardly extending circumferential bevel 52 extending from an area spaced from cylindrical inner surface 34 to cylindrical outer surface 36. Cylindrical inner surface 34 of ring member 14 is adapted to mate with bevel 52. In the preferred embodiment of FIGS. 1–4, bead 50 extends inwardly from inner surface 34 at second edge 46 and is adapted to mate with first with bevel 52. Thus, film 30 is free from direct pressure at bevel 52 during the mounting operation of ring member 14 and film 30 to holder body 12.

Holder body 12 is made of a rigid material such as a rigid plastic material such as a medium to high density polyethylene. Ring member 14 is made of a semi-rigid yet flexible, biasable material such as a biasable plastic such as a medium density to a high density polyethylene. Ring member 14 is thin-walled so as to retain a biasable characteristic. In general it may be noted that the thicker the wall of ring member 14, the less is its flexibility and the greater is its biasability. The degree of flexibility and biasability of ring member 14, which characteristics are in turn dependent on the type of material, the density of the material, and the thickness of the ring member 14, are such that the pressure exerted upon film 30 and on its film skirt 32 around both cylindrical outer surface 36 and at the circumferential bend of film 30 at second circular edge 26 of holder body 12 at open face 28 is a balance of firmness yet gentleness. The diameter of sample holder 10 varies in accordance with the analysis demands, and in order to maintain the same balance of gentleness and biasing pressure against film 30, the thickness of ring member 14 will likewise vary.

FIG. 5 illustrates holder body 12, ring member 14, and film 30 separated into individual elements immediately prior to assembly into the sample holder 10 shown in FIGS. 1–5. As indicated in FIGS. 1–5, ring member 14 is biasable between unbiased and biased modes, the unbiased mode being wherein ring member 14 has an unbiased inner surface 34 having a first diameter and the biased mode being wherein ring member 14 has a biased inner surface 34 having a diameter greater than the diameter of the unbiased inner surface 34. Holder body 12 has a cylindrical outer surface 36 having a diameter slightly greater than the diameter of unbiased inner cylindrical surface 34 of ring member 14 and substantially the same as biased inner surface 34 of ring member 14, wherein film 30 is biasedly gripped in locked relationship between holder body 12 and ring member 14 at the first locking position.

The step-by-step operation of the assembly of sample holder 10 including holder body 12, ring member 14, and film 30 in preparation for holding a sample for X-ray analysis is described below. It is noted that FIG. 5 shows sample holder 10 in preparation for the assembly with holder body 12 and ring member 14 inverted relative to their orientation shown in FIGS. 1–4. X-ray analysis directs X rays upward through film 30, which lies across open face 28, but the assembly process requires that the orientation of holder body 12 be reversed with open face 28 on the top side and ring member 14 be held over holder body 12 and open face 28. For this reason second circular edges 26 and 46 of holder body 12 and ring member 14, respectively, which are shown facing downwardly in FIGS. 1–4, are shown oriented facing upwardly in FIG. 5, where second circular edge 26 in particular is also upper circular rim 26 of cylindrical wall 18.

The method of assembly of sample holder 10 is as follows:

(a) placing in an upward disposition open face 28 of cell 20 of sample holder body 12 having cylindrical wall 18 forming cell 20, cylindrical wall 18 forming a bevel 52 extending outwardly and downwardly from upper rim 26, which forms open face 28;

(b) positioning a single layer sheet of thin transparent plastic film 30 across open face 28 of cell 20;

(c) drawing film skirt 32 downwards around cylindrical outer surface 36 of cylindrical wall 18 of holder body 12;

(d) gently sliding biasable cylindrical ring member 14, which has a cylindrical inner surface diameter (indicated as ISD in FIG. 5) in the unbiased mode substantially the same as the diameter of the cylindrical outer surface of holder body 12 (indicated as OSD in FIG. 5), onto bevel 52 of upper rim 26 of holder body 12 and around film skirt 32 and around upper rim 26 of cylindrical wall 18 of holder body 12, which has an cylindrical outer surface 36 having a diameter slightly greater than the diameter of inner surface 34 of ring member 14, thus forcing biasable ring member 14 to expand to a biased mode against film skirt 32 and cylindrical outer surface 36;

(e) gently sliding ring member 14 downward around cylindrical wall 18 of holder body 12 and over film skirt 32;

(f) gently drawing film skirt 32 away from open face 28 of holder body 12 and downwardly along cylindrical outer surface 36 of holder body 12 and so drawing film 30 taut across open face 28; and (g) sliding ring member 14 further downwardly over holder body 12 and positioning annular bead 42 extending inwardly from cylindrical inner surface 34 of ring member 14 into snap-in connection with annular locking groove 40 formed in cylindrical outer surface 36 of holder body 12, thus locking ring member 14 and film skirt 32 to holder body 12 at a first locking position around the common mating cylindrical surfaces 34 and 36 of holder body 12 and ring member 14, respectively, and further positioning ring member 14 at locking groove 40 and locking bead 42 at a second locking position that prevents axial movement of ring member 14 relative to holder body 12.

Circumferential bead 50 of ring member 14 extends inwardly from inner surface 34 proximate to second edge 46, and circumferential locking groove 48 is formed in outer surface 36 of holder body 12 proximate to upper rim 26. Another step simultaneous with step (g) is that of positioning bead 50 into connection with locking groove 48 thus locking ring member 14 and film skirt 32 to holder body 12 at a third locking position that prevents ring member 14 from moving axially relative to holder body 12.

Figure 4:
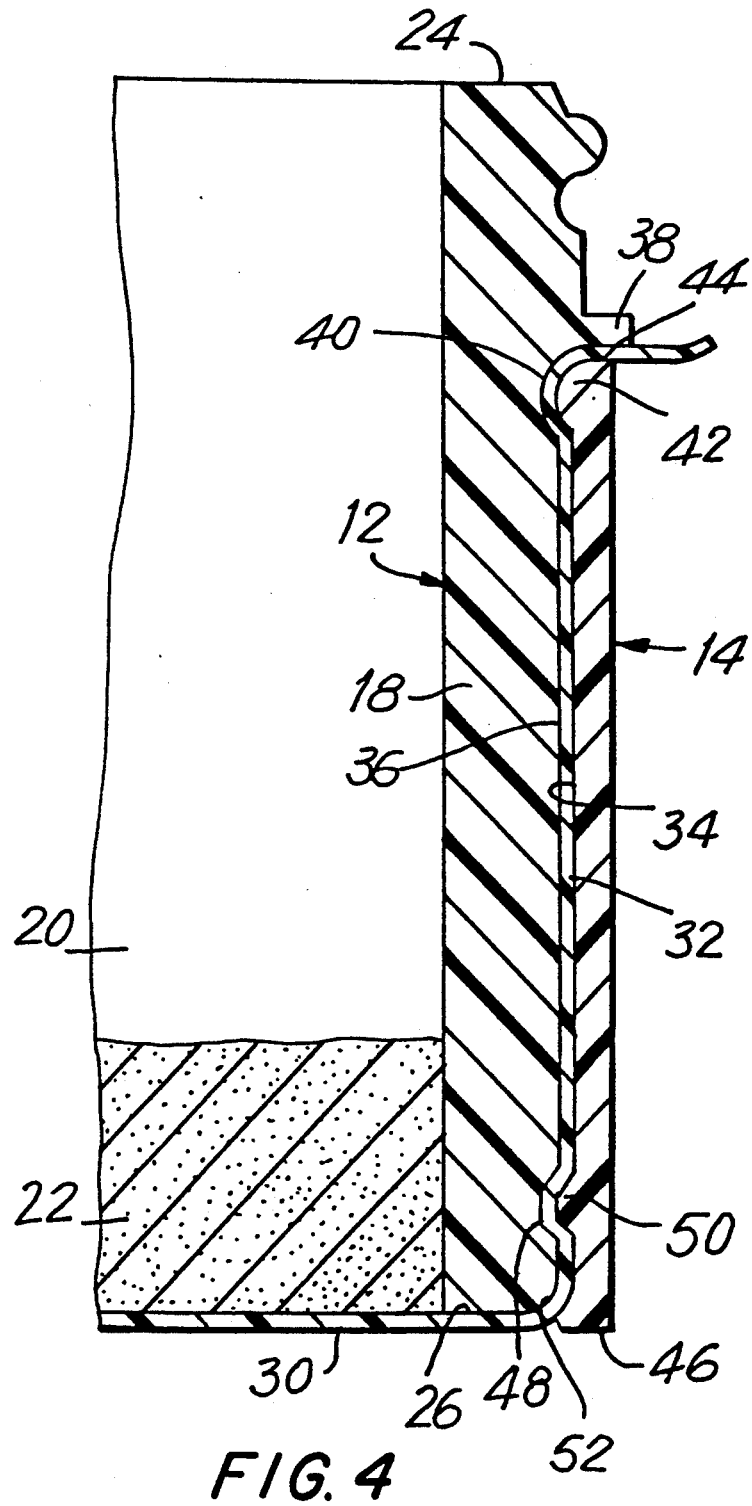
FIG. 4 is an enlarged view taken of the right segment of the sectional view of the sample holder shown in FIG. 3.

FIGS. 1–3 illustrate optional cap 16 snap-in mounted to the top portion of holder body 12. Cap 16 includes a top hand grip 54 and holder body forms a circumferential snap-in groove 56 for a circumferential bead (not shown) of cap 16. The type of cap 16 illustrated herein is for purposes of exposition only and cap 16 can be any of various types of caps known in the art, or sample holder 10 can for certain purposes be used without a cap.

The embodiments of the invention particularly disclosed here are presented merely as examples of the invention. Other embodiments, forms, and modifications of the invention coming within the proper scope of the appended claims will, of course, readily suggest themselves to those skilled in the art. For example, the cylindrical surfaces of holder body 12 and ring member 14 are traced by mating circular curves but could be traced by other types of mating curves, for example, ovals.

What is claimed is:

1. A film handling, positioning, and locking system for a sample holder for sample materials for spectroscopic analysis, comprising, in combination:

a body having a cylindrical wall comprising a cylindrical outer wall surface and a cylindrical inner wall surface defining therein a cell adapted to contain the sample material, said cylindrical wall having a circumferential first edge defining an open face of said cell, said cylindrical wall of said body having an outer diameter of a first predetemined value, film means positioned around said first edge and across said open face of said cylindrical wall for sealing said open face for the sample analysis, said film means including a film skirt for engagement with said cylindrical wall outer wall surface of said body, and cylindrical ring means having a cylindrical inner wall surface, the inside diameter of said cylindrical ring means having a second predetermined value less than said first predetermined value, when in its unbiased mode, said cylindrical ring means for biasedly pressing said film skirt against said cylindrical outer wall surface of said cylindrical wall of said body in a first locking position wherein said film skirt is tightly held between substantially the entire cylindrical outer wall surface of said cylindrical wall of said body and substantially the entire inner wall surface of said cylindrical ring means, said biasedly pressing being created by the attempted return of said ring means to its unbiased cylindrical mode to an inside diameter of said second predetermined value after said inside diameter has been increased to at least said first predetermined value to place ring means in its biased mode by the assembly of said ring means over said body and said film means; said ring means also positioning said film skirt relative to said cylindrical wall at a second locking position that prevents said ring means from moving axially from its position around said cylindrical wall of said body; said ring means also maintaining said film means across said open face of said cell sufficient to maintain a taut surface of said film means across said open face without imposition of undue strain upon said film.

2. The system according to claim 1 wherein said ring means includes a cylindrical outer surface and wherein said ring means for pressing said film means in a second locking position is a first annular bead extending radially inwardly formed on said cylindrical inner surface and a first annular groove extending radially inwardly from said outer surface of said body, said first annular bead being snap-in mounted into said first annular groove, said film skirt being pressed into said first annular groove by said first annular bead.

3. The system according to claim 2, further including means for stopping said ring means from moving axially inwardly relative said open face of said body.

4. The system according to claim 3, wherein said cylindrical wall of said body has a second edge defining an additional open face of said cell, said means for stopping is an annular flange extending radially outward from said cylindrical outer surface of said body, said ring means having opposed inner and outer circular ends, said outer end being coextensive with said first edge, said inner end being positioned adjacent to said flange.

5. The system according to claim 4, wherein said second locking position is located adjacent to said flange and said inner end of said ring means.

6. The system according to claim 5, wherein said ring member also includes means for positioning said film skirt relative to said cylindrical wall at a third locking position that prevents said ring member from moving axially from its position around said cylindrical wall of said body.

7. The system according to claim 6, wherein said means for positioning said film skirt in a third locking position is a second annular groove formed in said cylindrical outer surface of said body and a second annular bead extending radially inwardly from said cylindrical inner surface of said ring means, said second bead being snap-in mounted into said second annular groove, said film skirt being pressed into said second annular groove by said second annular bead, said third locking position being located in proximity to said first edge of said body.

8. The system according to claim 7, wherein said cylindrical wall of said body is beveled adjacent said first edge outwardly and downwardly from said inner cylindrical surface to said outer cylindrical surface, said second annular bead of said ring means mates with said outward bevel, wherein said cylindrical wall of said ring means mates with said bevel during the mounting operation.

9. The system according to claim 1, wherein said biasable ring means is made of a biasable plastic material.

10. The system according to claim 9, wherein said plastic material is polyethylene.

11. The system according to claim 9, wherein said plastic material is polypropylene.

12. A method for mounting film to a sampler holder body for holding a sample for analysis by X-ray, comprising the following steps:

(a) placing in an upwardly disposition an open face of a cell of a sample holder body having a cylindrical wall forming the cell, the cylindrical wall having a bevel extending outwardly from the upper rim of the cylindrical wall;

(b) positioning a single layer sheet of thin transparent plastic film across the open face of the cell;

(c) drawing the skirt of the film downwards around the cylindrical outer surface of the wall of the holder body;

(d) sliding a biasable, cylindrical ring means, which has a cylindrical inner surface having a diameter in the unbiased mode substantially the same as the diameter of the cylindrical outer surface of the holder body, onto the bevel of the upper rim of the holder body and around the skirt of the sheet of film and around the upper rim of the holder body, the cylindrical holder body having a cylindrical outer surface having a diameter slightly greater than the diameter of the cylindrical inner surface of the ring means, and forcing the biasable ring means to expand to a biased mode wherein the diameter of the ring means inner surface at least equals the diameter of the cylindrical outer surface of said holder body to create a biased pressure against the film skirt and the cylindrical outer surface of the holder body as the ring means attempts to return to its unbiased mode;

(e) sliding the ring means downwardly around the cylindrical wall of the holder body and over the film skirt;

(f) drawing the film skirt away from the open face of the holder body and downwardly along the cylindrical outer surface of the holder body to draw the film taut across the open face of the holder body; and (g) sliding the ring member further downwardly over the holder body and positioning an annular bead extending inwardly from the cylindrical inner surface of the ring means into snap-in connection with an annular locking groove formed in the cylindrical outer surface of the holder body, thus locking the ring means and the film skirt to the holder body at a first locking position around the common cylindrical mating surfaces of the holder body and the ring means, and further positioning the ring means at the locking groove and locking bead at a second locking position so as to prevent axial movement of the ring means relative to the holder body.

13. The method according to claim 12, wherein the ring means has another annular bead extending inwardly from the cylindrical inner surface proximate the second edge, and another annular groove is formed in the cylindrical outer surface of the holder body spaced from the second edge; further including the step of positioning the ring means with the another locking groove and another adjacent the locking bead at a third locking position simultaneous with positioning of said locking groove and said locking bead at a second locking position so as to prevent the ring means from sliding axially relative to the holder body.

* * * * *